United States Patent [19]
Godleski et al.

[11] Patent Number: 5,326,873
[45] Date of Patent: Jul. 5, 1994

[54] PALLADIUM CATALYZED ADDITION OF AMINES TO 3,4-EPOXY-1-BUTENE

[75] Inventors: Stephen A. Godleski, Fairport; Yann Hung, Rochester, both of N.Y.

[73] Assignee: Eastman Kodak Company, Rochester, N.Y.

[21] Appl. No.: 893,725

[22] Filed: Jun. 5, 1992

[51] Int. Cl.$^5$ ............... C07D 295/00; C07D 211/20; C07D 207/04; C07D 213/00

[52] U.S. Cl. ................... 544/401; 544/59; 544/170; 546/248; 548/341.1; 548/574; 564/474; 564/475; 564/477; 564/487; 564/503; 564/505; 564/506

[58] Field of Search ............ 544/401, 59, 170, 401; 546/248; 548/574, 341.1; 564/477, 503, 506, 474, 475, 477, 487, 505, 506, 503

[56] References Cited

U.S. PATENT DOCUMENTS

| | | | |
|---|---|---|---|
| 2,497,553 | 2/1950 | Long | 564/506 |
| 2,533,085 | 12/1951 | Blicke | 564/503 |
| 4,224,251 | 9/1980 | Mueller et al. | 564/503 |
| 4,272,455 | 6/1981 | Cook et al. | 564/503 |
| 4,321,271 | 3/1982 | McDonald | 564/503 |
| 4,897,498 | 1/1990 | Monnier et al. | 549/534 |
| 4,950,773 | 8/1990 | Monnier et al. | 549/534 |

OTHER PUBLICATIONS

Ettlinger, J.A.C.S. 72, 4792-4795 (1950).
Tsuji et al., Tetrahedron Letters 22, 2575-2578 (1981).
Trost et al., J.A.C.S. 108, 6053-6054 (1986).
Trost et al., J.A.C.S. 100, 7779 (1978).
B. M. Trost et al., "A Synthesis of Substituted Pyrrolidines via a Palladium(2+)-Catalyzed Cyclization. An Unusual Approach to a Carbapenem," 108 J. Amer. Chem. Soc 6053-6054 (1986).
B. M. Trost et al., "Steric Steering with Supported Palladium Catalysts," 100 J. Amer. Chem. Soc. 7779-7781 (1978).
J. Tsuji et al., "Regioselective 1,4–Addition of Nucleophiles to 1,3-Diene Monoepoxides Catalyzed by Palladium Complex," 22 Tetrahedron Letters 2575-2578 (1981).
B. M. Trost et al., "Neutral Alkylations via Palladium(0) Catalysis," 103 J. Amer. Chem. Soc. 5969-5972 (1981).
B. M. Trost et al., "Regiochemical Directing Efforts in Palladium Catalyzed Alkylations with Polyene Electrophilic Partners," 27 Tetrahedron Letters 4949-4952 (1986).
J. Tsuji et al., "Palladium-Catalyzed Regioselective Reactions of Silyl-Substituted Allylic Carbonates and Vinyl Epoxide," 29 Tetrahedron Letters 343-346 (1988).
J. Tsuji, "New Synthetic Reactions Catalyzed by Palladium Complexes," 58 Pure & Applied Chem. 869-878 (1986).
T. Tsuda, "Palladium-Catalyzed Reaction of 1,3-diene Monoepoxides with β-keto Acids. Allylic Alkylation and Isomerization of 1,3-Diene Monoexpodes," 51 J. Org. Chem. 5216-5221 (1986).
A. Tenaglia et al., "Palladium-catalyzed Reaction of 1,3-diene Monoepoxides with Sodium Azide," 29 Tetrahedron Letters 4851-4854 (1988).

*Primary Examiner*—Cecilia Tsang
*Attorney, Agent, or Firm*—J. Frederick Thomsen

[57] ABSTRACT

A method of forming 4-amino-2-buten-1-ol using 3,4-epoxy-1-butene is disclosed. A nitrogen nucleophile (e.g., an amine) is reacted with 3,4-epoxy-1-butene in the presence of a polymer-bound complex of palladium having up to four phosphine ligands.

20 Claims, No Drawings

PALLADIUM CATALYZED ADDITION OF AMINES TO 3,4-EPOXY-1-BUTENE

FIELD OF INVENTION

A process is disclosed for reacting 3,4-epoxy-1-butene with an amine to produce a 4-amino-substituted-2-buten-1-ol. The catalyst is a polymer-bound complex of palladium with up to four phosphine ligands.

BACKGROUND OF THE INVENTION

A variety of 4-aminobutenols are known to have use themselves or as intermediates for the preparation of other chemical substances. For example, 4-dimethylamino-2-buten-1-ol could be used in the preparation of 4-dimethylaminobutyraldehyde diethyl acetal, an intermediate for a pharmaceutical compound, as disclosed in German Pat. No. 3,700,408.

3,4-Epoxy-1-butene (butadiene monoepoxide) is one potential substrate for the production of 4-aminobutenols. However, the reaction of nitrogen nucleophiles (e.g., amines) with 3,4-epoxy-1-butene typically yields a mixture of the 1,2 addition product (1,2 adduct) and the 2,1 addition product (2,1 adduct), and little or none of the 1,4 addition product (1,4 adduct). The reaction is illustrated below:

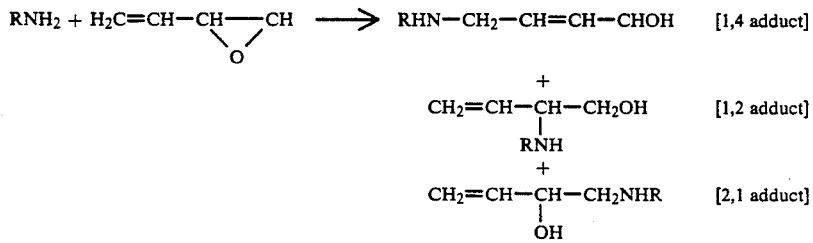

See, e.g., M.G. Ettlinger, "Synthesis of the Natural Antithyroid Factor 1-5-Vinyl-2-Thiooxazolidone", 72 J. Amer. Chem. Soc. 4792–4795 (1950); U.S. Pat. No. 2,533,085 to Blicke; W.B. Wheatley, et al., "o-Benzylphenyl Derivatives. IV. beta-Chloro-ethylamines", 72 J. Amer. Chem. Soc. 1655–1659 (1950); M.P. Crozet and W. Kassar, "Synthesis and Radical Cyclization of Benzazepinoethane Thiols", 99 Compte Rendu Acad. Sci. Paris 99–101 (1985); U.S. Pat. No. 2,497,553 to Long, Jr.; A.A. Petrov and V.M. Albitskaya, "The Reaction of Divinyloxide with Amines", 26 Zhur. Obshchei Khim. 2125–2127 (1956); and F.F. Blicke and J.H. Biel, "Aminolysis Products of 1-Chloro-2-Hydroxy-3-butene, 1-Hydroxy-2-Chloro-3-butene and 1,2-Epoxy-3-butene", 79 J. Am. Chem. Soc'y 5508–12 (1957).

The regioselective addition of nitrogen nucleophiles to substrates to form 4-aminobutenols (the 1,4 adduct product) is extremely unpredictable in both result and yield. For example, in Tsuji, et al., "Regioselective 1,4-Addition of Nucleophiles to 1,3-Diene Monoepoxides Catalyzed by Palladium Complex", 22 Tetrahedron Letters 2575-78 (1981) the formation of the 1,4 adduct from the palladium catalyzed reaction of 3,4-epoxy-1-dodecene and pyrrolidine is disclosed. Also, Trost, et al., "A Synthesis of Substituted Pyrrolidines via a Palladium(2+) Catalyzed Cyclization. An Unusual Approach to a Carbapenem", 108 J. Amer. Chem. Soc. 6053-54 (1986) discloses the formation of the 1,4 adduct from the addition of a nitrogen nucleophile to 3,4-epoxy-1-butene. On the other hand, Tsuda, et al., "Palladium(0)-Catalyzed (Reaction of Methyl-γ, δ-epoxysorbate with Nitrogen Nucleophiles", 54 Journal of Organic Chemistry 977–979 (1989) discloses that the palladium-catalyzed reaction of methyl-γ, δ-epoxysorbate with nitrogen nucleophiles is not regioselective for the 1,4 adduct.

It is widely recognized that the control of regiochemistry in the addition of nucleophiles to an intermediate unsymmetrical allyl-palladium substrate is an extremely complex problem. Many factors enter into the determination of which terminus of the electrophilic allyl ligand the nucleophile will preferentially attack. These factors include the steric nature of the nucleophile (see B.M. Trost, et al., "Allylic Alkylation: Nucleophilic Attack on pi-Allyl palladium Complexes", 100 J. Amer. Chem. Soc. 3416 (1978)) and the allyl substrate (see E. Keinen, et al. "Regioselectivity in Organo-transition-metal Chemistry. A Remarkable Steric Effect in pi-Allyl Palladium Chemistry", J. Chem. Soc., Chem. Commun., 648 (1984)); the electronic nature of the allyl substrate on the palladium (see J. Tsuji, et al., "Palladium-Catalyzed Regioselective Reactions of alpha-Acetoxy-beta, gamma,-Unsaturated Nitriles and gamma-Acetoxy-alpha, beta-Unsaturated Ester with Nucleophiles, "22 Tetrahedron Letters 2573 (1981)); the electronic nature of the other ligands on the palladium (see B. Akermark, et al., "Reactivity and syn-anti Isomerization of eta-3-geranyl and eta-3-neryl Palladium Complexes. Evidence for Electronic Control of the Regiochemistry of Nucleophilic Addition", 4 Organometallics 1275 (1985)); and the mechanism of the addition of the nucleophile (see Godleski, et al., "(pi-Allyl)-Palladium Complexes of Norcamphene. Structure and Reactivity", 3 Organometallics 21 (1984)).

B. Trost and E. Keinan, "Steric Steering with Supported Palladium Catalysts", 100 J. Amer. Chem. Soc. at 7779 (1978) ("Keinan") discloses that using a polymer-bound catalyst may have some effect on the stereoselectivity of primary amine addition to cis-3-acetoxy-5-carbomethoxy-1-cyclohexene. However, the relationship of stereochemistry and regiochemistry is very complex and unpredictable. See, e.g., B.M. Trost, 4 Comprehensive Organic Synthesis 585–662 (1991) ("Trost") (discussing nucleophiles with allyl metal complexes). In addition, regiochemical control of the amination of allyl-palladium complexes is known to be particularly unpredictable. See, e.g., B. Akermark, et al., "Amination of pi-Allylpalladium Chloride Complexes. A Mechanistic Study", 103 J. Amer. Chem. Soc. 3037–3040 (1981).

Keinan also discloses that the use of a polymer-bound catalyst may have some effect on the regioselectivity of the addition of carbon nucleophiles to sorbyl acetate. However, amine nucleophiles often behave quite differently than carbon nucleophiles, as discussed in Trost. This fact, as well as the chemical disparity between sorbyl acetate and 3,4 epoxybutene, leave in doubt what effect a polymer-bound catalyst might have on the addition of amines to 3,4-epoxybutene.

Therefore, in light of the usefulness of 4-amino-substituted-2-buten-1-ols derived from 3,4-epoxy-1-butene and the inherent unpredictability of the result (relative to both the product and the yield) of attempted regioselective amine additions to 3,4-epoxy-1-butene, there continues to be a need for predictable, efficient synthetic processes for deriving 4-amino-substituted-2-buten-1-ols from 3,4-epoxy-1-butene. Even small relative increases in the yield of the 1,4 adduct from amine addition to 3,4-epoxy-1-butene can translate into large cost savings when the increase is extrapolated out to production scale.

SUMMARY OF THE INVENTION

A process for producing improved yields of 4-amino-substituted-2-buten-1-ols is disclosed. More particularly, the palladium-catalyzed 1,4 addition of amines to 3,4-epoxy-1-butene is described. The present process includes the steps of providing a quantity of 3,4-epoxy-1-butene and a quantity of an amine and reacting the quantities of 3,4-epoxy-1-butene and the amine in a reaction medium and in the presence of a catalyst under conditions effective to form 4-amino-substituted-2-buten-1-ol. The method of the present invention utilizes is the use of a catalyst that is a polymer-bound complex of palladium with up to four phosphine ligands.

The present invention provides a method for forming 4-amino-substituted-2-buten-1-ols in yields that, especially at production levels, are significantly improved. In addition, the present method allows recovery of the catalyst. These factors combine to provide an improved, more cost-effective process for producing 4-amino-substituted-2-buten-1-ols.

DETAILED DESCRIPTION OF THE INVENTION

The process of the present invention relates to the formation of 4-amino-substituted-2-buten-1-ols from 3,4-epoxy-1-butene. The process includes the steps of providing a quantity of 3,4-epoxy-1-butene and a quantity of an amine. The amine and the 3,4-epoxy-1-butene are reacted in a medium in the presence of a catalyst. The catalyst is a complex of palladium with up to four phosphine ligands. At least one phosphine ligand has a substituent which is a polymer.

The 3,4-epoxy-1-butene used in the present method can be synthesized by any conventional process. Preferred processes for the preparation of 3,4-epoxy-1-butene are disclosed in U.S. Pat. Nos. 4,897,498 to Monnier et al. and 4,950,773 to Monnier et al.

The amines which will react with 3,4-epoxy-1-butene to form 4-amino-2-buten-1-ol include any lower primary amine, secondary amine, and heterocyclic amine. Primary amines useful in the present method have the general formula $R_1$-$NH_2$, wherein $R_1$ is a substituted or unsubstituted alkyl group having from one to twenty carbons. Examples of useful primary amines include alkylamines (e.g., methylamine, ethylamine, butylamine, hexylamine, octylamine, decylamine, and the like), alkenylamines (e.g., allylamine, 2-hexenylamine, 4-decenylamine, and the like), alkanolamines (e.g., ethanolamine, octanolamine, and the like), arylamines (e.g., aniline and the like), and cycloalkylamines (e.g., cyclohexylamine, cyclopentylamine, and the like).

Secondary amines useful in the present method have the general formula

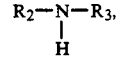

wherein $R_2$ and $R_3$ are each a substituted or unsubstituted alkyl group having from one to twenty carbons or a substituted or unsubstituted aryl group having from six to ten carbons, and $R_2$ and $R_3$ can be the same or different. Examples of useful secondary amines include dialkylamines (e.g., ethylmethylamines, diethylamines, butylpropylamines, di-n-propylamines, isobutylpropylamines, dihexylamines, octylhexylamines, and the like), dialkenylamines (e.g., allylhexenylamines, diallylamines, and the like), dialkanolamines (e.g., diethanolamine, and the like), N,N'-dialkylalkylenediamines (e.g., N,N'-di-methylethylenediamine, and the like), and dicycloalkylamines (e.g., dicyclohexylamine, cyclopentylhexylamine, and the like).

Cyclic amines are also useful secondary amines. Preferably, the cyclic amines are in the form of six-membered rings. Exemplary cyclic amines include morpholine, piperidine, pyrrolidine, N-methylpiperazine, hexamethyleneimine, and thiomorpholine. The cyclic amine may contain additional hetero-atoms including nitrogen, oxygen or sulfur.

The catalyst used in the present invention is a polymer-bound complex of palladium with up to four phosphine ligands. Palladium is in its zero oxidation state. Palladium in its zero oxidation state can be used directly or palladium(II) can be used, provided that it generates palladium(0) in situ. Each phosphine ligand provides a tri-substituted phosphorous atom (P) bonded directly to the palladium atom (Pd). At least one phosphine ligand also has one substituent which is a polymer. It is possible for more than one polymer bound phosphine to be ligated to the metal. A palladium atom in a zero oxidation state in a complex is assigned ten valence electrons. It requires eight additional electrons in order to attain an inert gas configuration. This configuration can be achieved by the donation of two electrons by each of four phosphine ligands. However, palladium (0) complexes can exist with only three phosphine ligands (16 electrons) or, to a lesser extent, with two phosphine ligands (14 electrons) and be stable and catalytically active. The catalysts useful in the present method can have the following general formula:

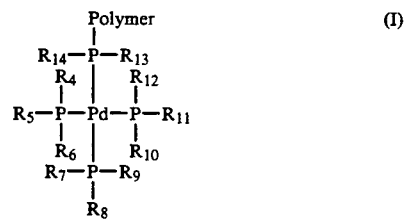

wherein $R_4$, $R_5$, $R_6$, $R_7$, $R_8$, $R_9$, $R_{10}$, $R_{11}$, and $R_{12}$, (collectively "$R_4$-$R_{12}$") can be the same or different and are substituted or unsubstituted hydrocarbons, preferably with no more than one of $R_4$-$R_{12}$") containing more than seven carbon atoms. In an especially preferred embodiment, $R_4$-$R_{12}$ are all phenyl moieties. $R_{13}$ and $R_{14}$ can be the same or different and are substituted or unsubstituted hydrocarbons. Preferably $R_{13}$ and $R_{14}$ are phenyl, tolyl, or a heterocyclic such as furyl.

In addition to the general formula above, two phosphines can be bound at the same polymer site to form a bidentate ligand according to formula II:

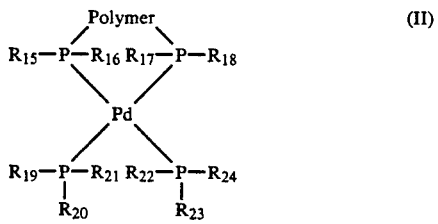

wherein $R_{19}$, $R_{20}$, $R_{21}$, $R_{22}$, $R_{23}$, and $R_{24}$, (collectively "$R_{19}$-$R_4$") can be the same or different and are substituted or unsubstituted hydrocarbons, preferably with no more than one of $R_{19}$-$R_{24}$ containing more than seven carbon atoms. In an especially preferred embodiment, $R_{19}$-$R_{24}$ are phenyl moieties. $R_{15}$, $R_{16}$, $R_{17}$, and $R_{18}$ can be the same or different and are substituted or unsubstituted hydrocarbons. Preferably, $R_{15}$, $R_{16}$, $R_{17}$, and $R_{18}$ are phenyl, tolyl, or a heterocyclic such as furyl.

Exemplary polymers to which the palladium catalyst can be bound include Polystyrene and, most preferably, diphenylphosphine derivatized polystyrene beads crosslinked with divinylbenzene as disclosed in B.M. Trost and E. Keinen, "Steric Steering with Supported Palladium Catalysts", 100 J. Am. Chem. Soc. 7779 (1978) ("Trost") and C.U. Pittman and Q. Ng, "Use of Polymer Matrices to Activate Palladium(0) Catalysts and Reduce Catalyst Agglomeration", 153 J. Organomett. Chem. 85 (1978), the disclosures of which are hereby incorporated by reference. Preferably, polystyrene beads used as a support for the palladium catalyst in the present method should be about 15–300 μm in diameter, most preferably about 35–250 μm. It is also advantageous, although not required, to crosslink the polystyrene beads with divinylbenzene. Divinylbenzene can be added in a concentration of about 1–10 weight percent ("wt %"), preferably about 8–10 wt %. Preferably, the ratio of phosphine to palladium on the polystyrene bead is in the range of from about 1:1 to about 20:1, as determined by Inductively Coupled Plasma Atomic Emission Spectrometry. Most preferably, the phosphine to palladium ratio on the bead can be from about 3:1 to 6:1. The polystyrene beads can be made by suspension polymerization as described in P. Hodge and D.C. Sherrington, *Polymer-Suooorted Reactions in Organic Synthesis*, Appendix, 469–75 (1980). Suitable polystyrene beads are also commercially available as Cat. No. 4020, 200–400 mesh, from polysciences, Inc., Warrington, PA.

The following references disclose exemplary processes useful in forming diphenylphosphine derivatized polystyrene beads crosslinked with divinylbenzene: "Supported Transition Metal Complexes as Catalysts", 15 Adv. Organomet. Chem. 189 (1977) (procedure for washing the beads); "[Poly(styryl)bipryidine] palladium(0)-Catalyzed Isomerization of Quadricyclene", 43 J. Org. Chem. 2958 (1978) (procedure for bromination of the beads); "Comparative Study of Some Selected Reactions of Homogeneous and Polymer-Supported Lithium Diorganocuprates", 44 J. Org. Chem. 2705 (1979) (procedure for phosphorylation of the beads); 153 J. Organomet. Chem. 85 (1978), 100 J. Am. Chem. Soc. 7779 (1978) (procedure for loading palladium on the beads).

Palladium(0) species can also be supported on: alumina, silica gel according to the method described in Trost; polyvinyl chloride, polybutadiene, or polyvinyl alcohol as described in K.G. Allum et al., "Supported Transition Metal Complexes I. Organic Polymers as the Support", 87 J. Organomet. Chem. 189 (1975); a copolymer of styrene, methacrylate, and ethylene 1,2-dimethacrylate (a cross-linking monomer) as described in R. Deschenaux, J. Stille, "Transition-Metal-Catalyzed Asymmetric Organic Synthesis via Polymer-Attached Optically Active Phosphine Ligands. 13. Asymmetric Hydrogenation with Polymer Catalysts Containing Primary and Chiral Secondary Pendant Alcohols", 50 J. Org. Chem. 2299 (1985), as well as other copolymers; or on cellulose as described in "Effect of Acid on the Radiation-Induced Copolymerization of Monomers to Cellulose", 11 J. Polym. Sci., Polym. Lett. Ed. 711 (1973). An example of a useful commercially available palladium complex supported on a polymer substrate is polymer-supported tetrakistriphenylphosphinepalladium(0), Catalog No. 24815-0, available from Aldrich Chemical Co., Inc.

The polymer bound catalyst of the present invention not only increases the yield of the 1,4 adduct, but has the additional advantage of protecting the catalyst against loss in use by facilitating extraction of the catalyst from the reaction system.

A wide variety of common organic liquid solvents can be used as the reaction medium in the inventive method. Useful solvents include tetrahydrofuran, diethyl ether, toluene, dimethylformamide, benzene, dimethylsulfoxide, chloroform, dichloromethane, acetonitrile, dioxane, alcohols, 1,2-dimethoxyethane, and acetone. Tetrahydrofuran is a particularly useful solvent because of its volatility which makes it easier to remove after the reaction. Tetrahydrofuran is also able to swell polymer beads to make them accessible to the reactants as well as ligate (and thereby stabilize) the metal.

The amount of the amine incorporated into the solvent can vary up to the amine's solubility limit. Preferably, the concentration of amine in the solvent is from about 0.1 to about 6 M, most preferably about 3 to about 6 M. In fact, the proportions of the reactants and the catalyst can be varied widely while obtaining the desired reaction product in high yield. Generally, because palladium is a precious metal, low concentrations of catalyst are preferred. Catalyst concentrations as low as 0.01 mole percent, based on 3,4-epoxy-1-butene, can be used. Preferably, the catalyst concentration is at least about 0.05 mole percent, most preferably at least about 0.1 mole percent, based on 3,4-epoxy-1-butene. The catalyst concentration is normally less than 20 mole percent, preferably less than 10 mole percent, based on 3,4-epoxy-1-butene.

The molar ratio of amine to 3,4-epoxy-1-butene can also vary over wide ranges. Molar ratios from 1:10 to 50:1, preferably 1:5 to 40:1, can be used. To maximize the conversion of 3,4-epoxy-1-butene, a stoichiometric excess of the remaining reactant or reactants should be present. Therefore, a particularly preferred range of amine to 3,4-epoxy-1-butene is in the range from about 3:1 to 40:1.

The conversion of 3,4-epoxy-1-butene can occur in a temperature range from about 0° C. to 125° C. Preferably, the reaction is performed at room temperature, although mild heating can be used to accelerate the reaction. The methylamine partial pressure can be up to 3 atmospheres.

The invention is further illustrated by the following examples.

EXAMPLES

Example 1

Reaction of 3,4-epoxy-1-butene and diethylamine (catalyzed with unbound catalyst)

5.0 g (4.3 mmole) of unbound tetrakistriphenylphosphine palladium(0) was dissolved in 20 ml tetrahydrofuran ("THF") under a nitrogen atmosphere. The solution was cooled to 0° C. 10 g (0.14 mole) diethylamine and 10 g (0.14 mole) 3,4-epoxy-1-butene were then added. The reaction mixture was stirred at room temperature for 36 hours. The reaction mixture was concentrated by evaporation at reduced pressure. The residue was distilled at reduced pressure. The reaction resulted in an 80% yield of a complex mixture of products. The product was analyzed by capillary gas chromatography ("GC") (HP 5893A Gas Chromatograph, DB5 column, 0.32 mm I.D., 0.25 micron thick, 30 meter, from J & W Scientific). Gas chromatography analysis revealed an approximately 1:1 mixture of 4-(N,N-diethylamino)-2-buten-1-ol (1,4 adduct) and 3-diethylamino-2-buten-4-ol (1,2 adduct).

Example 2

Reaction of 3,4-epoxy-1-butene and diethylamine (catalyzed with polymer-bound catalyst)

0.4 g of polymer-bound triphenylphosphine palladium(0) from Aldrich Chemical Co., Inc., Milwaukee, Wisconsin, Catalogue No. 24815-0 was suspended in 20 ml of THF, followed by 1.42 ml (14.3 mmol) diethylamine and 1.15 ml (14.3 mmol) 3,4-epoxy-1-butene. The reaction mixture was stirred at room temperature for 36 hours. The catalyst was removed by filtration and the filtrate was concentrated by evaporation at reduced pressure. The residue was distilled at reduced pressure. The reaction resulted in an 80% yield of 4-(N,N-diethylamino)-2-buten-1-ol. None of the isomeric 1,2 adduct was detected. The increased ratio of 4-(N,N-diethylamino)-2-buten-1-ol produced as compared to the approximately 1:1 ratio seen in Example 1 (with an unbound catalyst) has tremendous manufacturing advantages when extrapolated out to production scale synthesis.

Example 3

Reaction of 3,4-epoxy-1-butene and piperazine 1.23 g (14.3 mmol) of piperazine was dissolved in 20 ml of THF. 0.8 g of the polymer-bound palladium catalyst of Example 2 and 2.3 ml (28.6 mmol) 3,4-epoxy-1-butene was then added to the reaction mixture. The reaction mixture was stirred for 24 hours at room temperature. The catalyst was removed by filtration and the filtrate was concentrated at reduced pressure, resulting in a 98% yield of N,N'-di-(4-hydroxy-2-butenyl)-piperazine (1,4 adduct). None of the isomeric 1,2 adduct was detected.

Example 4

Reaction of 3,4-epoxy-1-butene and ethylaminoethanol 0.4 g of the polymer-bound palladium(0) catalyst of Example 2 was suspended in 20 ml of THF. 1.39 ml (14.3 mmol) of ethylaminoethanol and 1.15 ml (14.3 mmol) of 3,4-epoxy-1-butene was added to the reaction mixture. The reaction mixture was stirred for forty-eight hours at room temperature. The catalyst was removed by filtration and the filtrate was concentrated at reduced pressure to yield 85% of the 1,4 adduct, 4-(2-hydroxyethylamino)-2-buten-1-ol (1,4 adduct) with a 2:1 ratio of the trans type olefin to the cisoid olefin) (E:Z ratio of 2:1) and 15% of the 1,2 adduct, 3-(2-hydroxyethylamino)-1-buten-4-ol.

Example 5

Reaction of 3,4-epoxy-1-butene and piperidine 6.07 g (0.071 moles) of piperidine and 5.0 g (0.071 moles) 3,4-epoxy-1-butene were dissolved in 50 ml of THF. 1.0 g of the polymer-bound palladium(0) catalyst of Example 2 was then added to the reaction mixture. The resulting slurry was stirred at room temperature for 18 hours. The catalyst was removed by filtration and the filtrate was concentrated at reduced pressure. The residue was distilled at reduced pressure to yield 49.7% 4-(1-piperidino)-2-buten-1-ol (1,4 adduct) and 9% 3-(1-piperidino)-1-buten-4-ol (1,2 adduct).

Example 6

Reaction of 3,4-epoxy-1-butene and N,N'-diethylphenylenediamine 7.45 g (0.045 mole) of N,N'-diethylphenylenediamine and 6.36 g (0.091 mole) 3,4-epoxy-1-butene were dissolved in 70 ml of THF. The polymer-bound palladium(0) catalyst of Example 2 was then added to the reaction mixture. The resulting slurry was heated at reflux at 65° C. for 48 hours. The catalyst was removed by filtration and the filtrate was concentrated at reduced pressure. The residue was distilled at reduced pressure to yield
N,N'-[diethyl-di-(4-hydroxy-2-butenyl)]-phenylenediamine (1,4 adduct) and
N,N'-[diethyl-di-3-(4-hydroxy-1-butenyl)]-phenylenediamine (1,2 adduct) in a 4:1 ratio.

Example 7

Reaction of 3,4-epoxy-1-butene and imidazole 1.95 g (0.0286 moles) of imidazole and 2.0 g (0.0286 moles) of 3,4-epoxy-1-butene were dissolved in 25 ml of THF. 0.83 g of the polymer-bound palladium(0) catalyst of Example 2 was then added to the reaction mixture. The reaction mixture was stirred at room temperature for 24 hours. The catalyst was removed by filtration and the filtrate was concentrated at reduced pressure. The residue was distilled. The reaction Yielded about 95% 4-(1-imidazoYl)-2-buten-1-ol (1,4 adduct) and less than 5% 3-(1-imidazoyl)-1-buten-4-ol (1,2 adduct). The combined yield of products was 63%.

Example 8

Reaction of 3,4-epoxy-1-butene and methylamine (catalyzed with unbound palladium catalyst)

0.05 g (0.043 mmole) of unbound tetrakistriphenylphosphine palladium(0) was dissolved in a solution of 2.7 ml methylamine in THF (2.8 M) under an argon atmosphere. 0.06 ml (0.75 mmole) of 3,4-epoxy-1-butene was then added and the reaction mixture was stirred at 30° C. for 20 hours. The products of the reaction were approximately 60% 2,5- and 2,6-divinyldioxane. A low yield (7.4%) of the desired product, 4-methylamino 2 buten-1-ol, was present. Approximately 16% of the 1,2 adduct, 2-methylamino-3-buten-1-ol was formed. Therefore, the regioselectivity of the reaction (the ratio of the 1,4 adduct to the 1,2 adduct) was only about 0.45:1.

Example 9

Reaction of 3,4-epoxy-1-butene and methylamine (catalyzed with polymer-bound palladium catalyst)

A palladium catalyst bound to diphenylphosphine derivatized polystyrene beads was prepared according to the procedures disclosed in "Supported Transition Metal Complexes as Catalysts", 15 Adv. Organomet. Chem. 189 (1977) (procedure for washing the beads); "[Poly(styryl)bipryidine]palladium(0)-Catalyzed Isomerization of Quadricyclene", 43 J. Org. Chem. 2958 (1978) (procedure for bromination of the beads); "Comparative Study of Some Selected Reactions of Homogeneous and Polymer-Supported Lithium Diorganocuprates", 44 J. Org. Chem. 2705 (1979) (procedure for phosphorylation of the beads); 153 J. Organomet. Chem. 85 (1978), 100 J. Am. Chem. Soc. 7779 (1978) (procedure for loading palladium on the beads). The polystyrene beads, purchased from Polysciences, Inc., Cat. No. 4020, 200–400 mesh, were crosslinked with 2 wt % divinylbenzene. The beads were about 37–74 $\mu$m in diameter and contained 8.4 wt % phosphine and 4.5 wt % palladium (0.042 mmole). The weight ratio of P to Pd was 6:1. 0.1 g of supported palladium catalyst was swelled in 2.7 ml methylamine in THF (2.8 M) under an argon atmosphere for 1 hour. 0.06 ml (0.75 mmole) of 3,4-epoxy-1-butene was then added. The reaction mixture was stirred at 30° C. for 20 hours. The product was analyzed by GC. 2,5- and 2,6-divinyldioxane were not detected in the product. The major products were 4-methylamino-2-buten-1-ol and 2-methylamino-3-butene-1-ol. The regioselectivity of the reaction for the desired 4-methylamino-2-buten-1-ol was 1.8:1. A comparison of this result with Example 8 (unbound catalyst) shows a much higher regioselectivity for the 1,4 adduct when a polymer-bound catalyst is used.

Example 10

Reaction of 3,4-epoxy-1-butene and methylamine catalyzed with polymer bound catalyst 3,4-epoxy-1-butene and methylamine were reacted according to the process described in Example 9, except that the polystyrene beads used as a support were crosslinked with 8 wt % divinylbenzene. The reaction yielded the desired 4-methylamino- 2-buten-1-ol and some 2-methylamino-3-butene-1-ol. The regioselectivity of the reaction for the desired 1,4 adduct increased to 2.3:1 as compared to Example 9 where the divinylbenzene concentration was 2 wt % divinylbenzene. Example 11

Reaction of 3,4-epoxy-1-butene and methylamine catalyzed with polymer bound catalyst 3,4-epoxy-1-butene and methylamine were reacted according to the process described in Example 9, except that the phosphine to palladium ratio on the polystyrene beads was 15. The reaction yielded the desired 4-methylamino-2-buten-1-ol and some 2-methylamino-3-butene-1-ol. The regioselectivity of the reaction for the desired 1,4 adduct was 1.6:1.

Example 12

Reaction of 3,4-epoxy-1-butene and methylamine catalyzed with polymer bound catalyst 3,4-epoxy-1-butene and methylamine were reacted according to the process described in Example 9, except that the polystyrene beads used as a support had a diameter of 15 $\mu$m. The reaction yielded the desired 4-methylamino- 2-buten-1-ol and some 2-methylamino-3-butene-1-ol. The regioselectivity of the reaction for the desired 1,4 adduct was 1.3:1. This was a decrease compared to Example 9 (1.8:1) where 37–74 $\mu$m diameter beads were used.

Example 13

Reaction of 3,4-epoxy-1-butene and methylamine catalyzed with polymer bound catalyst A palladium catalyst bound to 2,3-O-isopropylidene-2,3-dihydroxy-1,4-bis(diphenyl-phosphino)butane ("DIOP") derivatized polystyrene beads was prepared according to the procedures described in W. Dumont, "Assymetric Catalytic Reduction With Transition Metal Complexes", 95 J. Am. Chem. Soc. 8295 (1973) (synthesis of DIOP derivatized polystyrene beads); B.M. Trost and E. Keinen, "Steric Steering with Supported Palladium Catalysts", 100 J. Am. Chem. Soc. 7779 (1978) ("Trost") (loading palladium onto beads); and C.U. Pittman and Q. Ng, "Use of Polymer Matrices to Activate Palladium(0) Catalysts and Reduce Catalyst Agglomeration", 153 J. Organomett. Chem. 85 (1978) (loading palladium onto beads). The resulting catalyst contained 3.1 wt % palladium. Methylamine and 3,4-epoxy-1-butene were then reacted in the presence of the synthesized catalyst according to the procedure of Example 9. The regioselectivity of the reaction for the desired 4-methylamino-2-buten-1-ol was 1.5:1.

Example 14

Reaction of 3,4-epoxy-1-butene and methylamine catalyzed with polymer bound catalyst A palladium catalyst bound to di-para-tolylphosphine derivatized polystyrene beads was prepared. The di-para-tolylphosphine derivatized polystyrene beads were prepared according to the procedure described in Example 9 except that lithium (di-para-tolyl)phosphide was substituted for lithium diphenylphosphide in the procedure for phosphorylation of the polystyrene beads. Palladium was loaded onto the beads by the procedure described in Example 9. The resulting catalyst contained 2.9 wt % palladium. Methylamine and 3,4-epoxy-1-butene were then reacted in the presence of the synthesized catalyst according to the procedure of Example 9. The regioselectivity of the reaction for the desired 4-methylamino-2-buten-1-ol was 1.6:1.

Example 15

Reaction of 3,4-epoxy-1-butene and methylamine catalyzed with polymer bound catalyst A palladium catalyst bound to tri-2-furylphosphine derivatized chloromethylated polystyrene beads was prepared. Initially, chloromethylated polystyrene beads were crosslinked with 3 wt % divinylbenzene. Next, 3.39 g of tri-2-furylphosphine was dissolved in 80 ml of ether. 5.7 ml of a 2.5 M solution of n-butyl lithium in cyclohexane was added to this solution and the resulting mixture was stirred for two hours. This mixture was transferred to 2 g of chloromethylated polystyrene beads which had been swelled in 20 ml of tetrahydrofuran for one hour. This mixture was stirred for 18 hours, refluxed for one hour, cooled, and quenched with a 3:1 acetone/water mixture. The derivatized chloromethylated polystyrene beads were successively filtered and washed as follows: water (twice), 1:1 acetone/water mixture (once), acetone (twice), dichloromethane (twice), benzene (twice), and methanol (twice). The filtered beads were dried at 50° C. and 0.5 mm Hg for 18 hours. Palladium was loaded onto the beads by the procedure described in Example 9. The resulting catalyst contained 3.1 wt % palladium. Methylamine and 3,4-epoxy-1-butene were then reacted in the presence of the synthesized catalyst according to the procedure of Example 9. The regioselectivity of the reaction for the desired 4-methylamino-2-buten-1-ol was 1.4:1.

Example 16–19

Effect of amine concentration on regioselectivity of polymer-bound palladium catalyzed reaction of 3,4-epoxy-1-butene and an amine 3,4-epoxy-1-butene and methylamine were reacted according to the process described in Example 9, except that 0.35 ml (0.43 mmole) of 3,4-epoxy-1-butene was used in each example and the amount of methylamine used was varied to provide the stated methylamine to 3,4-epoxy-1-butene ratio. The methylamine was varied by diluting a 6 M methylamine in THF solution by adding additional THF to provide the desired methylamine to 3,4-epoxy-1-buten ratio. The experimental details and results are shown in Table I below. "[MeNH$_2$:EpB]"is the methylamine to 3,4-epoxy-1-butene ratio and "[1,4]:[1,2]" is the regioselectivity of the reaction for the 1,4 adduct.

TABLE I

| Example | MeNH$_2$ (ml) | THF (ml) | [MeNH$_2$:EpB] | [1,4]:[1,2] |
|---|---|---|---|---|
| 13 | 0.36 | 2.54 | 5:1 | 1.6:1 |
| 14 | 0.73 | 2.18 | 10:1 | 1.8:1 |
| 15 | 1.45 | 1.45 | 20:1 | 1.9:1 |
| 16 | 2.9 | 0 | 40:1 | 2.0:1 |

Table I indicates as the amine concentration increases relative to the epoxide, the regioselectivity of the amine addition for the desired 1,4 adduct increased, as indicated by the ratio of 1,4 to 1,2 adduct formed.

Although the invention has been described in detail for the purpose of illustration, it is understood that such detial is solely for that purpose, and variations can be made therein by those skilled in the art without departing from the spirit and scope of the invention which is defined by the following claims.

What is claimed is:

1. A process of forming N-substituted-4-amino-2-buten-1-ol comprising the steps of:
   providing a quantity of 3,4-epoxy-1-butene;
   providing a quantity of an amine; and
   reacting said quantity of 3,4-epoxy-1-butene with said amine in a reaction medium and in the presence of a catalyst consisting essentially of a bound complex of palladium with up to four phosphine ligands to form N-substituted-4-amino-2-buten-1-ol, wherein said palladium is bound to a support selected from the group consisting of polystyrene, polystyrene beads crosslinked with divinylbenzene, alumina, silica gel, polyvinyl chloride, polybutadiene, polyvinyl alcohol, copolymers of styrene and methacrylate, and cellulose.

2. The process according to claim 1, wherein said amine is selected from the group consisting of primary amines, secondary amines, and cyclic amines.

3. A process according to claim 2, wherein, said amine is selected from the group consisting of methylamine, diethylamine, piperzaine, piperidine, N,N'-diethyl-phenylenediamine, imidazole, and ethylaminoethanol.

4. A process according to claim 2, wherein said cyclic amine is a heterocyclic amine having one or more hetero-atoms.

5. A process according to claim 4, wherein said heterocyclic amine has at least two hetero-atoms, one of said hetero-atoms being nitrogen and one of said hetero-atoms being selected from the group consisting of oxygen, nitrogen, and sulfur.

6. A process according to claim 1, wherein said support consists essentially of polystyrene beads crosslinked with about 1 to 10 weight percent divinylbenzene.

7. A process according to claim 6, wherein said polystyrene beads have as diameter of from about 15 to 300 µm.

8. A process according to claim 7, wherein said polystyrene beads have a diameter of about 37–74 µm.

9. A process according to claim 6, wherein said polystyrene beads are crosslinked with about 8–10 weight percent divinylbenzene.

10. A process according to claim 6, wherein said phosphine is present on said bead relative to said palladium catalyst in a ratio in a range from about 1:1 to 20:1.

11. A process according to claim 10, wherein said ratio of phosphine to palladium on said bead is in a range from about 3:1 to 6:1.

12. A process according to claim 2, wherein said support consists essentially of polystyrene beads crosslinked with about 1 to 10 weight percent divinylbenzene.

13. A process according to claim 12, wherein said polystyrene beads are crosslinked with about 8–10 weight percent divinylbenzene.

14. A process according to claim 12, wherein said polystyrene beads have as diameter of from about 15 to 300 µm.

15. A process according to claim 12, wherein said phosphine is present on said bead relative to said palladium catalyst in a ratio in a range from about 1:1 to 20:1.

16. A process according to claim 15, wherein said ratio of phosphine to palladium on said bead is in a range from about 3:1 to 6:1.

17. A process according to claim 2, wherein said reaction medium is a solvent selected from the group consisting of tetrahydrofuran, diethyl ether, toluene, benzene, N,N-dimethylformamide, dimethyl sulfoxide, dioxane, ethyl alcohol, dichloromethane, and 1,2-dimethoxyethane.

18. A process according to claim 2, wherein said amine is present in said solvent in a range from about 0.1 to 10.0 M and in a molar ratio relative to said 3,4-epoxy-1-butene in the range from about 3:1 to 40:1, and the quantity of said catalyst is from about 0.1 to about 10 mole percent relative to the quantity of said 3,4-epoxy-1-butene.

19. A process for forming N-substituted 4-amino-2-buten-1-ol comprising:
providing a quantity of 3,4-epoxy-1-butene;
providing a quantity of an amine selected from the group consisting of methylamine, diethylamine, ethylaminoethanol, piperazine, piperidine, N,N-diethyl-phenylenediamine, and imidazole; and
reacting said quantity of 3,4-epoxy-1-butene with said amine in a solvent selected from the group consisting of tetrahydrofuran, diethyl ether, toluene, benzene, N,N-dimethylformamide, and dimethyl sulfoxide, and in the presence of a catalyst consisting essentially of a complex of palladium with up to four phosphine ligands bound to polystyrene beads to form N-substituted 4-amino-2-buten-1-ol, wherein said polystyrene beads have a diameter in the range of from about 15 to 300 $\mu$m and are cross-linked with 1-10 weight percent divinylbenzene, and the ratio of said phosphine to said palladium on said polystyrene beads is in the range of about 1:1 to 20:1.

20. A process for forming N-substituted-4-amino-2-buten-1-ol comprising the steps of:
providing a quantity of 3,4-epoxy-1-butene;
providing a quantity of an amine; and
reacting said quantity of 3,4-epoxy-1-butene with said amine in a reaction medium and in the presence of a catalyst consisting essentially of a bound complex of palladium with up to four phosphine ligands to form N-substituted-4-amino-2-buten -1-ol, wherein said catalyst has a formula selected from the group consisting of:

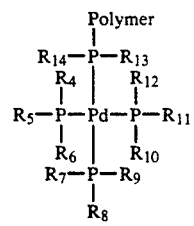

wherein $R_4$, $R_5$, $R_6$, $R_7$, $R_8$, $R_9$, $R_{10}$, $R_{11}$, and $R_{12}$ are the same or different and are substituted or unsubstituted hydrocarbons with no more than one of $R_4$-$R_{12}$ having more than seven carbon atoms, and $R_{13}$ and $R_{14}$ are phenyl, tolyl, or furyl, and said polymer includes a repeating unit which is a polyaromatic compound and

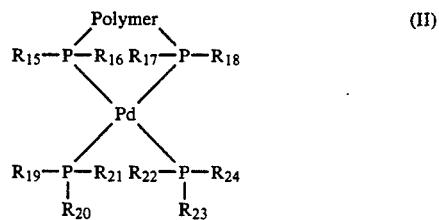

wherein $R_{19}$, $R_{20}$, $R_{21}$, $R_{22}$, $R_{23}$, and $R_{24}$ are the same or different and are substituted or unsubstituted hydrocarbons with no more than one of $R_{19}$-$R_{24}$ having more than seven carbon atoms, and $R_{15}$, $R_{16}$, $R_{17}$, and $R_{18}$, are phenyl, tolyl, or furyl and said palladium is bound to a support selected from the group consisting of polystyrene, polystyrene beads cross-linked with divinylbenzene, alumina, silica gel, polyvinyl chloride, polybutadiene, polyvinyl alcohol, copolymers of styrene and methacrycylate, and cellulose.

* * * * *